US00PP12686P2

(12) United States Plant Patent
Sherman et al.

(10) Patent No.: US PP12,686 P2
(45) Date of Patent: Jun. 11, 2002

(54) PEACH TREE NAMED 'GULFPRINCE'

(75) Inventors: Wayne B. Sherman, Gainesville, FL (US); Gerard W. Krewer, Tifton; Thomas G. Beckman, Byron, both of GA (US)

(73) Assignee: The United States of America as represented by the Secretary of Agriculture, Washinton, DC (US)

( * ) Notice: Subject to any disclaimer, the term of this patent is extended or adjusted under 35 U.S.C. 154(b) by 0 days.

(21) Appl. No.: 09/515,238

(22) Filed: Mar. 6, 2000

(51) Int. Cl.[7] ..... A01H 5/00
(52) U.S. Cl. ..... Plt./197
(58) Field of Search ..... Plt./197

*Primary Examiner*—Bruce R. Campell
*Assistant Examiner*—Annette H. Para

(57) ABSTRACT

A new and distinct variety of peach tree which has a winter chilling requirement of approximately 400 chill units (cu). The tree is of large size, with a highly vigorous spreading growth habit, and has showy pink flowers. Glands are small and reniform in shape and isolated to the basal portions of leaves. This tree, which has been denominated 'Gulfprince' is a regular bearer of heavy crops of early mid-season fruit which are large for its ripening season. Fruit are very firm, yellow, non-melting flesh which are clingstone. Fruit are uniform, attractive, substantially symmetrical shape, and have an attractive 45 to 55% solid red skin. The fruit ripens 10 to 14 days after 'June Gold' in early June at Attapulgus, Ga.

1 Drawing Sheet

BACKGROUND OF THE NEW VARIETY

The present invention relates to a new and distinct variety of peach (*Prunus persica* (L.) Batsch) tree which is named 'Gulfprince' and, more particularly to a peach tree which produces highly colored, good eating quality, clingstone, non-melting flesh fruit which are mature for fresh market in early June at Attapulgus, Ga. and which are produced on a tree adapted to a semi-mild winter climate. Asexual propagation was performed through 2 successive buddings at Gainesville, Fla. where the selection was made and trees were tested at Gainesville and at Attapulgus. Asexually propagated plants remained true to type. Contrast is made to 'June Gold' (unpatented) peach, a standard variety, for reliable description. This new variety is a promising candidate for commercial success in that it retains fruit firmness at the full flavor, tree ripe stage for 10 days on the tree.

ORIGIN OF THE VARIETY

This peach tree (genotype) originated in the fruit breeding program at the University of Florida, located at Gainesville, Fla. The seed parent was 'Aztecgold' (unpatented), a non-melting flesh peach [originated as an $F_2$ of 'Sunred' (unpatented) nectarinex'Mexican Cling' (unpatented) peach]. The pollen parent was 'Oro A' (unpatented), a non-melting flesh peach that originated as a seed importation from Brazil. 'Gulfprince' peach was selected from about 50 sibs in 1993, it exhibited yellow, non-melting clingstone flesh, and was designated Fla. 93-14C. It was propagated as a uniform variety through standard asexual propagation by budding on 'Flordaguard' (unpatented) seedling rootstock for root-knot nematode control and determined at Attapulgus to have unique tree and fruit characteristics making it worthy for commercial fresh fruit production. There are no known effects of this rootstock on this scion cultivar.

SUMMARY OF THE VARIETY

The new and distinct variety of peach tree bears yellow, non-melting flesh fruit, and has a moderate-chilling dormancy requirement. 'Gulfprince' blooms about 10 days before 'June Gold' peach at Attapulgus, bearing red skin, non-melting and yellow flesh fruit. The estimated chilling requirement is 400 chill units as compared to 'June Gold' at 650 chill units.

The present invention resulting in 'Gulfprince' peach tree is characterized by non-melting flesh fruit of excellent flavor and eating quality on a tree adapted to medium chill winters. The trees are vigorous, productive and regular bearing. Trees attain in two years, a height of three meters and a spread of two meters at Attapulgus. Terminal growth of up to a meter annually is common on mature five-year-old trees with normal pruning to a vase shape. The first fruit ripen the first week of June at Attapulgus or in about 105 to 115 days from full bloom, which is about 10 to 14 days after 'June Gold'. The fruit are uniformly large for an early-mid season peach. Ripe fruit have 45 to 55% solid (no stripes) red skin with a small amount of red pigment throughout the flesh on the sun exposed side of the fruit, especially on trees stressed during hot, dry weather. There is no red pigment in the flesh at the pit. The showy flowers are pink and the anthers are light red to yellow, a common characteristic of many standard peach and nectarine varieties.

BRIEF DESCRIPTION OF THE DRAWINGS

The accompanying drawing is a color photograph which shows a typical specimen of the fruit, leaf, and stem of the new variety as nearly true as it is reasonably possible to make in a color illustration of this type. The photograph shows an attractive shape and exterior coloration of four specimens of fruit above a ruler in side view, stem end view, a blossom end view, and side view showing the suture.

DETAILED BOTANICAL DESCRIPTION

The tree, flowers, and fruit may vary in slight detail due to variations in soil type, cultural practices, and climatic conditions. The potential for commercial production of fresh fruit by 'Gulfprince' is high, due to its attractive red skin over a bright yellow ground color, large fruit of good flavor, and exceptional firmness due to its non-melting flesh. The present botanical description is that of the variety as grown on 5-year-old trees on 'Flordaguard' rootstock under the ecological conditions prevailing at Attapulgus, Ga. Colors are described from "The Pantone Book of Color" published by H. N. Abrams, Inc., N.Y. 1990.

Tree:

*Ploidy.*—Diploid.

*Size.*—Trees are large when trained to an open vase form.

*Vigor.*—Vigorous, and must be summer and winter pruned to keep tree height restricted and to keep center of vase open.

*Density.*—Medium to dense in branching habit.

*Form.*—Semi-upright when pruned to vase shape.

*Bearer.*—Regular, must be fruit thinned to avoid limb breakage and obtain large fruit size. Yields equivalent to 200 to 250 bushels (50 lbs. each) per acre on 4 and 5 year old trees have been obtained on hand thinned trees under a commercial simulated orchard culture at Attapulgus.

Trunk:

*Size.*—Large trunk diameter attaining 10 cm diameter at a height of 30 cm at the end of 3 years field growth at Attapulgus.

*Texture.*—Medium smooth, but changes to medium rough as tree ages.

*Bark color.*—Older bark gray, Lead Gray (Pantone 17-1118).

*Lenticels.*—Numerous (14 per 4 square inches of surface area of trunk), small (2–5mm radial length) with the center being Mineral Yellow (Pantone 15-1046).

Branches:

*Size.*—Strong growth of scaffold branches.

*Texture.*—Relatively smooth, medium amount of lenticels attaining size found on trunk and old scaffolds.

*Color.*—New wood is light green, Tarragon (Pantone 15-0326); Old wood is more brown, Ash (Pantone 16-3802).

*Crotch angles.*—Angles selected at 45 to 90 degrees in first year of tree training. Natural angles are within the normal range of standard varieties for a semi-upright tree.

Leaves:

*Size.*—Medium; 15 to 19 cm length, including the petiole; 3 to 4 cm width. Measurements were made on vigorous upright shoots of summer growth.

*Thickness.*—Regular and average for commercial peach varieties.

*Form.*—Lanceolate.

*Apex.*—Acute.

*Margin.*—Serrulate, slightly undulate.

*Base.*—Cuneate.

*Surface.*—Upper, glabrous; Lower, medium large veins.

*Color.*—Lower surface is green, Grasshopper (Pantone 18-0332); Upper surface is slightly darker green, Black Forest (Pantone 19-0315).

*Glands.*—Two to four small reniform glands mostly on lower leaf blade, but occassionally on petiole. Leaf glands are moderately smaller than those on most commercial varieties. Leaf glands on young leaves are light green darkening to brown on older leaves in mid-summer.

*Petiole.*—About 1 cm (0.7 to 1.1 cm).

*Stipules.*—Medium size and early deciduous.

Flower buds:

*Abundance.*—Moderately high, most buds produce flowers that set fruit in absence of spring frosts.

*Size.*—Medium, average 3.5 mm length.

*Form.*—Plump, conic.

*Surface.*—Pubescent scales.

*Color.*—Brown, Stucco (Pantone 16-1412) in late winter.

Flowers:

*Blossom period.*—10 days before 'June Gold' peach — average February 12–16 at Attapulgus.

*Aroma.*—Slight to none.

*Type.*—Showy, location and seasonally variable, and in the mid-range of commercial showy varieties. Freshly opened flowers averaged 1½ inches diameter. Texture is smooth.

*Color.*—Pink, darkening to pink red before abscising and within the range of standard commercial varieties.

*Flower parts.*—Stamens and pistil size and color are within the size and color range of standard commercial varieties. The number of sepals and petals are 5 as is common for all commercial varieties.

*Calyx cup.*—Medium small as compared to commercial varieties.

*Anthers.*—Light red to yellow, regular size.

*Pollen.*—Abundant and bright yellow (common to many varieties).

*Fertility.*—Fully self fertile, and no cross pollination is required.

Fruit:

*Maturity when described.*—Tree ripe, Jun. 4, 1999 at Attapulgus.

*Date of first picking.*—Jun. 1, 1999 at Attapulgus.

*Date of last picking.*—Jun. 10, 1999 at Attapulgus.

*Size.*—Uniform, medium large (large size for early mid-season maturity at 140 to 180 g). Average equatorial diameter. — 2½ inches (64 mm). Average polar length (stem to distal end). — 2¾ inches (70 mm).

Form:

*Longitudinal section form.*—Slightly oval.

*Transverse section through diameter.*—Round.

*Suture.*—Shallow and inconspicuous.

*Ventral surface.*—Rounded.

*Base.*—Slightly retuse.

*Apex.*—Round to slight point.

*Cavity.*—Flaring circular.

*Cavity depth.*—¼ to ⅜ inch (6 to 9 mm).

*Cavity breadth.*—5/32 inch (3 mm) at attachment.

Skin:

*Thickness.*—Medium in comparison to commercial peach varieties.

*Texture.*—Medium in comparison to commercial peach varieties.

*Tenacity.*—Tenacious to flesh.

*Color.*—Bright red, Fire Cracker (Pantone 16-1452) over 45 to 55% of skin. Ground color deep yellow, Radiant Yellow (Pantone 15-1058).

*Tendency to crack.*—None observed.

Flesh:

*Ripens.*—Evenly within each fruit and throughout the tree.

*Texture.*—Firm, juicy, non-melting when fully ripe.

*Fibers.*—Very fine, tender, small.

*Aroma.*—Moderate and in the middle range of commercial peach varieties.

*Eating quality.*—Good, sweet, slightly acid. Fruit averaged near 13 degrees brix on a refractometer when described at harvest date on Jun. 4, 1999. Titratable acidity was 0.83 as % malic acid and, standard for peach, penetrometer firmness was 1.6 Kg.

*Juice.*—Abundant.

*Color.*—Deep yellow, Saffron (Pantone 14-1064) with some redness throughout the flesh, especially on stressed trees under dry, hot conditions. There is no red at the pit.

*Browning by oxidation.*—Slight on soft ripe fruit.

*Amygdalin.*—Undetected.

Stone:

*Type.*—Clingstone, adhering to flesh even at softening.

*Size.*—Medium small; average length — 30 mm, average width — 23 mm.

*Color.*—Grey Sand (Pantone 13-1010) when freshly exposed.

*Form.*—Oblong.

*Base.*—Straight.

*Apex.*—Acute.

*Sides.*—Near equal.

*Surface.*—Irregularly furrowed toward the ventral edge.

*Ridges.*—Jagged toward the base.

*Pit wall.*—3/16 to ¼ inch thick (5 to 6 mm).

*Tendency to split.*—Low, none observed.

*Use.*—Fresh; dessert.

*Resistance to disease.*—High resistance to bacterial spot incited by *Xanthomonas campestris* pv. *pruni*. Resistance to other fruit and tree diseases are within the range for commercial peach cultivars in Florida.

*Keeping quality.*—Excellent after 2 weeks at 7 C.

*Shipping quality.*—Degree of firmness at harvest and firmness retained in refrigeration for 2 weeks at 7 C. indicates fruit should be highly acceptable for shipping.

We claim:

1. A new and distinct peach tree variety as illustrated and described, characterized by a mid-chilling requirement, and bearing early mid-season fruit having firm, yellow, non-melting flesh of high eating quality and an attractive, high percentage red overcolor with fruit ripening in early June or 10 to 14 days after June Gold at Attapulgus, Ga.

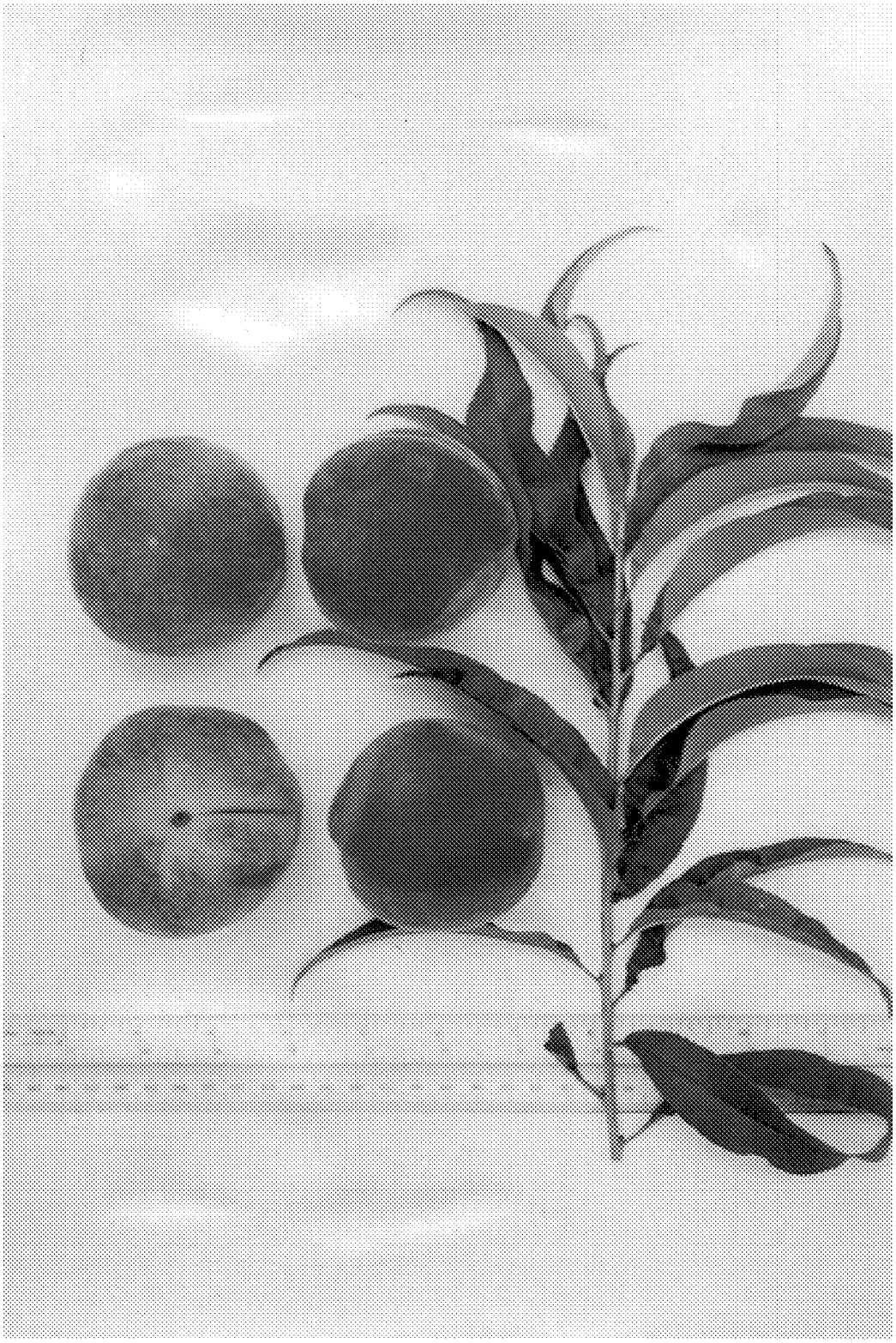

* * * * *